United States Patent
Markert et al.

(10) Patent No.: US 7,060,668 B2
(45) Date of Patent: Jun. 13, 2006

(54) 2,3, 5, 5-TETRAMETHYLHEXANAL DERIVATIVES

(75) Inventors: Thomas Markert, Monheim (DE); Volker Porrmann, Hilden (DE)

(73) Assignee: Kao Corporation, Tokyo (JP)

( * ) Notice: Subject to any disclaimer, the term of this patent is extended or adjusted under 35 U.S.C. 154(b) by 87 days.

(21) Appl. No.: 10/469,829

(22) PCT Filed: Feb. 26, 2002

(86) PCT No.: PCT/EP02/01994

§ 371 (c)(1),
(2), (4) Date: Feb. 10, 2004

(87) PCT Pub. No.: WO02/070466

PCT Pub. Date: Sep. 12, 2002

(65) Prior Publication Data

US 2004/0138092 A1    Jul. 15, 2004

(30) Foreign Application Priority Data

Mar. 7, 2001  (DE) .............................. 101 10 858

(51) Int. Cl.
*A61K 7/46*    (2006.01)

(52) U.S. Cl. ............................ 512/6; 558/435; 558/303
(58) Field of Classification Search ................... 512/6; 558/435, 303
See application file for complete search history.

(56) References Cited

U.S. PATENT DOCUMENTS 4,863,631 A * 9/1989 Sprecker et al. ........ 252/187.25

FOREIGN PATENT DOCUMENTS

| DE | 27 23 636 | 12/1978 |
|----|-----------|---------|
| DE | 36 32 398 | 3/1988 |
| DE | 39 32 325 | 4/1991 |
| WO | 01 85672 | 11/2001 |

* cited by examiner

*Primary Examiner*—Monique T. Cole
(74) *Attorney, Agent, or Firm*—Oblon, Spivak, McClelland, Maier & Neustadt, P.C.

(57) ABSTRACT

The invention relates to compounds of the general formula (1), wherein R represents a group CH═N—OH or a group CN. The inventive compounds are characterized by interesting and original odor characteristics which diffuse extremely well and are suitable for use as fragrances, for example in cosmetic preparations, technical products or in alcoholic perfumery.

6 Claims, No Drawings

2,3,5,5-TETRAMETHYLHEXANAL DERIVATIVES

FIELD OF THE INVENTION

The present invention relates to 2,3,5,5-tetramethylhexanal derivatives as well as the use thereof as fragrances.

PRIOR ART

Many natural fragrances are not available, in view of their demand, in sufficient amounts. For example, 5000 kilos of rose blossoms are necessary to yield 1 kg rose oil. The consequence is a greatly limited annual production worldwide as well as a high price. It is therefore clear that the fragrance industry has a constant need for new fragrances with interesting scents. On the one hand the range of naturally available fragrances can be supplemented thereby and on the other hand it is possible thereby to be able to undertake the necessary adaptation to the ever changing fashion in taste. Moreover it becomes possible by this means to be able to cover the ever increasing demand for scent enhancers for products of daily use, such as cosmetics and cleaning agents.

Moreover there is generally a constant demand for synthetic fragrances which can be produced inexpensively and with a uniform high quality and have the original olfactory characteristics. In particular they should have a pleasant scent profile which is as natural as possible, qualitatively novel, of sufficient intensity and capable of advantageously influencing the scent of cosmetic goods and goods of daily use. In other words: There is a constant demand for compounds which have a characteristic novel scent profile and at the same time a high degree of staying power, intensity of scent and a strong diffusion. 2,3,5,5-tetramethylhexanal and its use as a fragrance is known from German laid-open publication DE-A-27 23 623.

DESCRIPTION OF THE INVENTION

It was found that the compounds of the general formula (I) excellently fulfill the above-mentioned requirements in every way and can be used in an advantageous manner as fragrances with differing shades of smell and with good staying power.

The subject matter of the present invention is, initially, 2,3,5,5-tetramethylhexanal derivatives of the general structure (I)

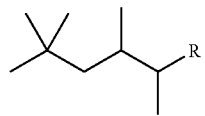

(I)

in which R denotes a residue —CH=N—OH or a residue —CN.

In a further embodiment, the invention relates to the use as fragrances of compounds of the general structure (I) designated above in detail.

The compounds (I) according to the invention, namely 2,3,5,5-tetramethylhexanal oxime and 2,3,5,5-tetramethylhexane nitrile are characterized by an odor characteristic in which currant and grapefruit scents dominate. They have excellent stability in formulations for cosmetics and perfume products of daily use.

The production of the compounds (I) can be carried out according to known synthesis methods of organic chemistry.

In perfume compositions the compounds (I) increase the harmony and the diffusion as well as the naturalness and also the staying power, with the dosage being adjusted to each smell targeted, taking the other components of the composition into consideration.

That the compounds (I) have the above-mentioned scents was not predictable and is thus a further confirmation of the general experience that the olfactory characteristics of known fragrances do not allow automatic conclusions to be drawn regarding the properties of compounds having related structures since neither the perception mechanism of smells nor the influence of the chemical structure on the perception of smell has been sufficiently researched, and thus normally it cannot be predicted whether an altered structure of known fragrances will result at all in a change of the olfactory characteristics and whether these changes will be positively or negatively assessed by the person skilled in the art.

The compounds of formula (I) are suited, due to their smell profile, in particular also for the modification and enhancement of known compositions. Their exceptional scent strength should in particular be emphasized, which contributes quite generally to the refinement of the composition.

The compounds of formula (I) can be combined with numerous known fragrance ingredients, for example other fragrances of natural, synthetic or partial-synthetic origin, essential oils and plant extracts. The range of natural fragrances can include thereby not only high-volatile but also middle- and low-volatile components. The range of the synthetic fragrances can include representatives of practically all substance classes.

Examples for suitable substances with which the compounds (I) can be combined are in particular:

(a) Natural products such as evernia furfuraceae (tree moss) absolute, basilicum oil, citrus oils such as bergamot oil, mandarin oil, etc., mastic absolute, myrtle oil, palmarosa oil, patchouli oil, petit grain oil, absinth oil, myrrh oil, olibanum oil, ceder wood oil, sandal wood oil, East Indian, guajak wood oil, cabreuva, (b) Alcohols such as farnesol, geraniol, citronellol, linalool, nerol, phenylethyl alcohol, rhodinol, cinnamyl alcohol, Sandalore [3-methyl-5-(2.2.3-trimethylcyclopent-3-en-1-yl)pentan-2-ol], Sandela [3-ioscamphyl-(5)-cyclohexanol], Muguetanol, (c) Aldehydes such as citral, Helional®, alpha-hexylcinnamylaldehyde, hydroxycitronellal, Lilial® [p-tert.-butyl-α-methyldihydrocinnamaldehyd], methylnonylacetaldehyde, (d) Ketones such as allyl ionone, α-ionone, β-ionone, Isoraldein, methyl ionone, noot katone, Calone, α-, β- and γ-Irone, Damascone, (e) Esters such as allyl phenoxyacetate, benzylsalicylate, cinnamylpropionate, citronellyl acetate, decylacetate, dimethylbenzylcarbinylacetate, ethylacetoacetate, hexenylisobutyrate, linalylacetate, methyldihydrojasmonate, vetiveryIacetate, cyclohexylsalicylate, isobornylisobutyrate, Evernyl, (f) Lactones such as gamma-undecalacton, 1-oxaspiro [4.4]nonan-2-on, cylopentadecanolide, ethylenbrassylate, (g) Ethers such as Herbavert, Ambroxan, as well as various further components often used in the perfume industry such as musk and sandal wood fragrances, indole, p-menthane-8-thiol-3-on, methyleugenol and methylanthranilate.

Noteworthy is furthermore how such compounds of structure (I) round off the scents of a wide range of known compositions and harmonize these without, however, being dominant in an unpleasant manner.

2,3,5,5-tetramethylhexane nitrile is characterized, together with excellent fragrance properties, by a good stability in alkaline media, such as soap or detergent, rinsing and cleaning agents. This stability is clearly better than that of 2,3,5,5-tetramethylhexanal.

The usable proportions of the compounds (I) according to the invention or their blends in fragrance compositions range from approximately 1–70% by wt., based on the entire mixture. Blends of the compounds (I) according to the invention as well as compositions of this kind can be used both to perfume cosmetic preparations such as lotions, creams, shampoos, soaps, ointments, powders, aerosols, toothpastes, mouthwash, deodorants as well as also in alcoholic perfumery (e.g. eau de cologne, eau de toilette, extracts). There is also the possibility for use to perfume technical products such as detergents and cleaning agents, fabric softeners and textile treating agents. To perfume these various products, the compositions are added to these in an amount effective olfactorally, in particular in a concentration of 0.01 to 2% by wt. based on the entire product. These values do not, however, constitute restrictive limits since the experienced perfumer can still attain effects with even lesser concentrations or can construct novel complexes with even higher dosages.

EXAMPLES

Production of 2,3,5,5-Tetramethylhexanal 2,3,5,5-tetramethylhexanal is used as raw material in the examples 1 and 2 given below. It is produced as follows:

Charge:
1) 78 g (0.5065 mol) 2-methylene-isononanal (produced according to FR 150 88 54)
2) 4 g 5% Pd/C hydrogenating catalyst (Degussa)
3) 100 ml ethanol, industrial Apparatus:
1 l hydrogenation autoklav box A 432 with steel insert and blade agitator.

Execution:
1), 3) and 2) were weighed out one after the other in the autoklav insert in inert gas (nitrogen) and placed in the pressure tank. After purging with nitrogen, the reaction mixture was treated with 30 bar hydrogen. An exothermal reaction took place, with the temperature of the mixture increasing from 17° to 40° C. After 2 hours reaction time, in which the pressure of the hydrogen was increased at 100° C. to 50 bar, the pressure remained constant for 5 hours at 50 bar. Thereafter it was cooled off, pressure was released, the catalyst filtered off and the reaction mixture on the rotary evaporator was freed of solvent. The conversion control showed a product concentration of 90.5% along with 2.4% educt.

62 g of the raw product was used for the distillation in a Vigreux column of 15 cm. 41.5 g main product with a purity, determined by gas chromatography, of 97% was obtained at 30–31° C./0.1 mbar.

Yield:
52.5% of the theoretical

Analysis:
The IR spectrum (film between NaCl) showed characteristic vibrational bands at 1727 (CO) and 2701 cm$^{-1}$.

The $^1$H-NMR (400 MHz in CDCl$_3$) showed 2 signals for 3 methyl groups (singulet target molecule+isomers in ratio 3:1) at 0.9 ppm, and 2 methyl groups at 0.9 ppm and 1.0 ppm (dublets). The signals of the CH$_2$ groups next to the two asymmetric C atoms were, as was to be expected, split more greatly with signal centers at 1.1 and 1.3 ppm (dublets of dublet, the signal at 1.3 ppm is accompanied by a corresponding signal of the probable by-component). The two methin protons (5 and 6 neighbor protons, respectively) appear at 2.0 and 2.3 ppm (multiplets, the signal at 2.0 ppm was accompanied by the corresponding signal at 2.1 ppm, the probable by-component). The aldehyde proton was present as weakly split dublet at 9.7 ppm (accompanied by a signal of the probable by-component). It is assumed in view of the spectroscopic evaluation that the by-component could be the 2,4,5,5-tetramethylhexanal.

Scent:
The first smell is dry, aldehydic, minty, green and the subsequent smell (after 24 hours on a scent strip) was slightly of Isononal.

Example 1

Production of 2,3,5,5-Tetramethylhexanal Oxime

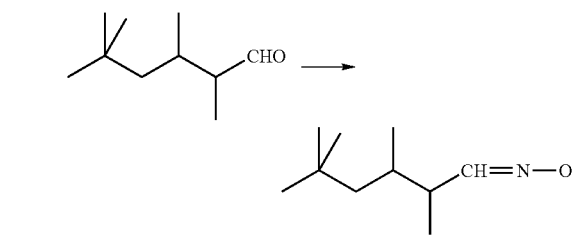

Charge:
1) 33 g (0.2 mol) hydroxlaminosulfate in 120 ml water
2) 12.0 g (0.3 mol) sodium hydroxide in 24 ml water
3) 41.5 g (0.266 mol) 2,3,5,5-tetramethylhexanal (97%), produced as described above Apparatus:
1 l 4-necked flask with agitator and drip funnel.

Execution:
1) was placed in the flask and 2) was added dropwise in 10 minutes while being stirred, the temperature increased thereby from 17 to 25° C. While being stirred and cooled with an ice bath, 3) was added by dosage in 35 minutes. Thereafter the mixture shows a light yellow coloration. The reaction mixture was heated to 80° C. and stirred for 6 hours at this temperature. After 6 hours the concentration of the product was 96%.

Further Processing:

The mixture was cooled and extracted twice with 200 ml ether each, the ether phases were washed with water and sodium sulphate solution (pH 6.5) and dried over night with sodium sulphate. The solvent was distilled off on the rotary evaporator and 46.4 g raw product was obtained as residue with a purity of 96%, determined with a gas chromatograph. The raw product was distilled on a bulb tube distillation means and 40 g of 97.2% product was obtained as main product:

Yield:
87.9% of the theoretical

Analysis:

The IR spectrum (film between NaCl) showed characteristic vibrational band groups at 939, 1394, 1477 and 2959 $cm^{-1}$ and a sack with a maximum at 3269 (OH) $cm^{-1}$.

The $^1$H-NMR (400 MHz in $CDCl_3$) showed signals for 3 methyl groups (1 singulet) at 0.9 ppm and for 2 methyl groups at 0.95 ppm and 1.05 ppm (dublets). The $CH_2$ group yielded dublets of dublets with geminal coupling at 1.0 and 1.3 ppm. At 1.7 and 2.3 ppm 2 multiplets appeared for the two protons at C-2 and C-3. The multiplet at 2.3 ppm was accompanied by a correspondingly split H at 3.05 ppm (for the by-component, probably 2,4,5,5-tetramethylhexanal oxime). The olefinic H gave a signal for the by-component at 6.6 ppm and a signal (dublet of dublet) at 7.35 ppm. The OH proton appeared (not exchanged) as broad signal with maximum at 7.8 ppm.

Scent Characteristic:

The first smell is flowery, sweet, fruity, of Chardonnay, white wine aroma, bitter, of grapefruit, currant and the subsequent smell (after 24 hours on a scent strip) was bitter, of grapefruit, cassis.

Example 2

Production of 2,3,5,5-Tetramethylhexane Nitrile

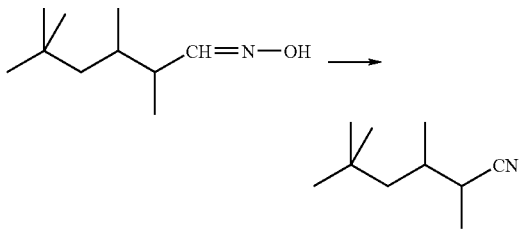

Charge:
1) 37.8 g (0.22 mol) 2,3,5,5-tetramethylhexanal oxime (97.2%) produced as described in example 1
2) 54.4 g (0.5 mol) acetanhydride Apparatus:
0.5 l 4-necked flask with agitator, PT 100 thermometer, 250 ml drop funnel and reflux cooler.

Execution:
1) was placed in the reaction vessel and while being stirred and cooled with an ice water bath 2) was added dropwise in 40 minutes. The temperature of the mixture increased thereby from 22° to 28° C. After the complete addition of 2) the mixture was heated to 140° C. for the reflux and stirred at this temperature for 2.5 hours. The conversion after 2 hours was 93%.

Further Processing:

The reaction mixture was diluted with 500 ml cyclohexane, washed neutral with 2.5 liters water, dried over magnesium sulphate and concentrated on a rotary evaporator. 34.5 g raw product was distilled in a Vigreux column of 15 cm, 22.4 g main product was obtained at 28–30° C./0.05 bar. The purity was 98.8%, as determined with a gas chromatograph.

Yield:
86.4% of the theoretical

Analysis:

The IR spectrum (film between NaCl) showed characteristic vibrational band groups at 1367, 1470 and 2958 $cm^{-1}$ and a band at 2239 (CN) $cm^{-1}$.

The $^1$H-NMR (400 MHz in $CDCl_3$) showed signals for 3 methyl groups (1 singulet) at 0.9 ppm, and for 2 methyl groups at 1.1 ppm and 1.3 ppm (dublets). The $CH_2$ group yielded dublets of dublets with geminal coupling at 1.1; 1.3 and 1.4 ppm. At 1.7 and 2.6 ppm 2 multiplets appeared for the two protons at C-2 and C-3. The multiplet at 2.6 ppm was accompanied by a correspondingly split H at 2.5 ppm (for the by-component, probably 2,4,5,5-tetramethylhexane nitrile).

Scent Characteristic:

The first smell is aldehydic, fresh, fruity, has an isononanal note, green, strong, and the subsequent smell (after 24 hours on a scent strip) is almost devoid of smell.

The invention claimed is:

1. A 2,3,5,5-Tetramethylhexanal derivative of formula (I),

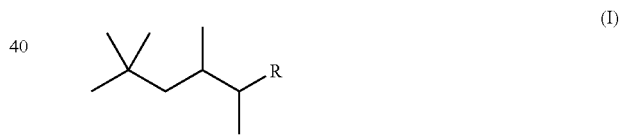

wherein R denotes a residue —CH=N—OH or a residue—CN.

2. A method of fragrancing comprising applying the 2,3,5,5-tetramethylhexanal derivative of claim 1.

3. A fragrance composition comprising the 2,3,5,5-tetramethylhexanal derivative of claim 1, wherein said composition comprises 1–70% by weight, based on the entire composition of said 2,3,5,5-tetramethylhexanal derivative.

4. The fragrance composition of claim 3, wherein said composition is in a form selected from the group consisting of a lotion, a cream, a shampoo, a soap, an ointment, a powder, an aerosol, a toothpaste, a mouthwash, a deodorant and an alcoholic perfumery.

5. The 2,3,5,5-Tetramethylhexanal derivative of claim 1 which is 2,3,5,5-tetramethylhexanal oxime.

6. The 2,3,5,5-Tetramethylhexanal derivative of claim 1 which is 2,3,5,5-tetramethylhexanal nitrile.

* * * * *